United States Patent [19]

Guillaume et al.

[11] 4,333,939
[45] Jun. 8, 1982

[54] TETRAHYDROPYRIDINYL-INDOLES

[75] Inventors: Jacques Guillaume, Sevran; Lucien Nedelec, Le Raincy; Claude Dumont, Nogent-sur-Marne, all of France

[73] Assignee: Roussel Uclaf, Paris, France

[21] Appl. No.: 163,967

[22] Filed: Jun. 30, 1980

[30] Foreign Application Priority Data

Jul. 13, 1979 [FR] France .................................. 79 18217
Mar. 7, 1980 [FR] France .................................. 80 05180

[51] Int. Cl.³ ..................... A61K 31/44; C07D 401/04
[52] U.S. Cl. ..................................... 424/263; 546/273
[58] Field of Search .......................... 546/273; 424/263

[56] References Cited

U.S. PATENT DOCUMENTS 3,980,658  9/1976  Passanza et al. .................... 546/273
3,993,764  11/1976  Dumont et al. ...................... 424/267
4,196,209  4/1980  Dumont et al. ...................... 546/273
4,232,031  11/1980  Dumont et al. ...................... 546/273

FOREIGN PATENT DOCUMENTS 2227873  11/1974  France .

OTHER PUBLICATIONS

Freter, J. Org. Chem. 1975, vol. 40 (17), pp. 2525-2529.

Primary Examiner—John M. Ford
Assistant Examiner—Natalia Harkaway
Attorney, Agent, or Firm—Hammond & Littell, Weissenberger and Muserlian

[57] ABSTRACT

Novel tetrahydro-pyridinyl-indoles of the formula

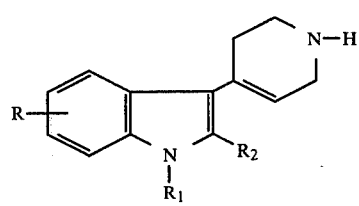

wherein R is selected from the group consisting of amino, trifluoromethyl and methylthio, $R_1$ and $R_2$ are individually selected from the group consisting of hydrogen and alkyl of 1 to 3 carbon atoms and their non-toxic, pharmaceutically acceptable acid addition salts having antidepressive, antiparkinson and antiemetic activity and their preparation.

3 Claims, No Drawings

TETRAHYDROPYRIDINYL-INDOLES

STATE OF THE ART

Literature relating to indole derivatives include French Patent No. 2,227,873, U.S. Pat. Nos. 4,195,081; 4,196,209 and 3,993,764, copending, commonly assigned U.S. patent application Ser. No. 2,453 filed Jan. 10, 1979 and J. Org. Chem., Vol. 40 (1975), No. 17. p. 2525.

OBJECTS OF THE INVENTION

It is an object of the invention to provide the novel indoles of formula I and their non-toxic, pharmaceutically acceptable acid addition salts and a process for their preparation.

It is a further object of the invention to provide novel antidepressively, antiemetically and antiparkinson effective compositions and to provide novel method of treating vomitting and depression and parkinson syndromes in warm-blooded animals.

These and other objects and advantages of the invention will become obvious from the following detailed description.

THE INVENTION

The novel compounds of the invention are selected from the group consisting of an indole of the formula

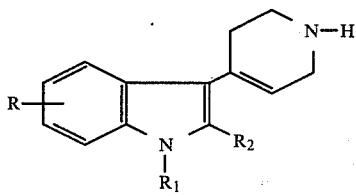

wherein R is selected from the group consisting of amino, trifluoromethyl and methylthio, $R_1$ and $R_2$ are individually selected from the group consisting of hydrogen and alkyl of 1 to 3 carbon atoms and their non-toxic, pharmaceutically acceptable acid addition salts. The group R may be in any position on the indole but is preferably in the 5- or 6-position, most preferably in the 5-position.

Examples of the substituents of formula I are alkyl of 1 to 3 carbon atoms such as methyl, ethyl, propyl and isopropyl.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkanesulfonic acids such as methanesulfonic acid and ethanesulfonic acid, arylsulfonic acids such as benzenesulfonic acid and p-toluene sulfonic acid and arylcarboxylic acids.

Among the preferred compounds of formula I are those wherein $R_1$ and $R_2$ are hydrogen and their non-toxic, pharmaceutically acceptable acid addition salts. A particularly preferred compound is 3-(1,2,3,6-tetrahydro-4-pyridinly)-5-methylthio-1H-indole and its non-toxic, pharmaceutically acceptable acid addition salts.

The novel process of the invention for the preparation of a compound of formula I comprises reacting a compound of the formula

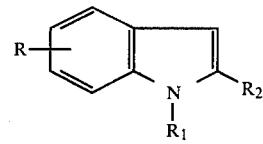

wherein R, $R_1$ and $R_2$ have the above definitions with 4-piperidone hydrochloride in an alkaline or acid media. The reaction is preferably effected in 2 N methanolic potassium hydroxide solution but equally useful are sodium hydroxide or an alkali metal alcoholate. The reaction is preferably effected at reflux. When the 1- or 2-position of the indole is substituted, the reaction is preferably effected in an acid media such as acetic acid.

The acid addition salts of formula I are prepared in the classical manner by reacting substantially stoichiometric amounts of the acid and the free base of formula I.

The novel therapeutic compositions of the invention are comprised of an antidepressively and antiparkinson and antiemetically effective amount of at least one compound of formula I and its non-toxic, pharmaceutically acceptable acid addition salts and an inert pharmaceutical carrier. The compositions may be in the form of tablets, dragees, gelules, granules, suppositories and injectable solutions or suspensions.

Examples of suitable excipients or pharmaceutical carriers are talc, arabic gum, lactose, starch, magnesium stearate, cacaco butter, aqueous and non-aqueous vehicles, fatty bodies of animal or vegetable origin, paraffinic derivatives, glycols, diverse wetting agents, dispersants or emulsifiers and preservatives. Among the preferred compositions of the invention are those wherein $R_1$ and $R_2$ are hydrogen and their non-toxic, pharmaceutically acceptable acid addition salts. A particularly preferred compound is 3-(1,2,3,6-tetrahydropyridin-4-yl)-5-methylthio-1H-indole and its non-toxic, pharmaceutically acceptable acid addition salts.

The compositions are useful for the treatment of psychic troubles, of behavior troubles and character troubles in the treatment of akinetic and dyskinetic states as well as for the treatment of vometting and nausea of all types.

The noval method of the invention for inducing neuroleptic, antiemetic and antipsychotic activity in warm-blooded animals, including humans, comprising administering to warm-blooded animals a sufficient amount of at least one compound of formula I and its non-toxic, pharmaceutically acceptable acid addition salts to induce antiemetic, antidepressive and antiparkinson activity. The compounds may be administered orally, rectally or parenterally. The usually daily dose is depending on the subject treated, the complaint concerned, the compound and the method of the administration. It may be, for example, 0.1 to 10 mg/kg daily, by oral route in the adult with the product of example I.

The compounds of formula II wherein R is methylthio may be prepared by reacting cuprous mercaptate with a compound of the formula

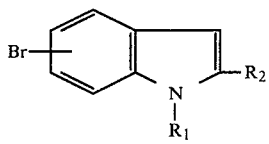

III

In the following examples there are described several preferred embodiments to illustrate the invention. However, it should be understood that the invention is not intended to be limited to the specific embodiments.

EXAMPLE 1

3-(1,2,3,6-tetrahydro-4-pyridinyl)-5-methylthio-1H-indole hydrochloride

STEP A: 5-methylthio-1H-indole

A mixture of 22.7 g 5-bromo-1H-indole of 230 ml of quinoline, 16 g of cuprous mercaptate [prepared by Engelhardt, J. Med. Chem. II (1968), p. 329] and 34 ml of anhydrous pyridine was refluxed with stirring for 5 hours and was then cooled and added to a mixture of 1 liter of 2 N hydrochloric acid and 1 liter of ethyl acetate. The mixture was filtered and the decanted organic phase was wahsed with 2 N hydrochloric acid and then with aqueous sodium chloride solution, dried and evaporated to dryness at 40° C. under reduced pressure. The 17.8 g of residue were chromatographed over silica gel and eluted with a 1-1 cyclohexane-benzene mixture to obtain 11.75 g of 5-methylthio-1H-indole.

| U.V. Spectrum (ethanol): | | |
|---|---|---|
| Max. at 225 nm | $E_1^1 = 1812$ | $\epsilon = 29,400$ |
| Inflex. towards 250 nm | $E_1^1 = 710$ | |
| Inflex. towards 278 nm | $E_1^1 = 249$ | |
| Inflex. towards 294 nm | $E_1^1 = 188$ | |
| Inflex. towards 310 nm | $E_1^1 = 98$ | |

STEP B: 3-(1,2,3,6-tetrahydro-4-pyridinyl)-5-methylthio-1H-indole hydrochloride A mixture of 22.1 g of the hydrate of 4-piperidone hydrochloride and 108 ml of 2 N methanolic potassium hydroxide solution was refluxed with stirring under an inert atmosphere for 16 hours and was cooled and poured into one liter of ice water. The mixture was stirred for 15 minutes and was filtered and the recovered product was washed with water, dried and crystallized from a 10-3 ethyl acetate-methanol mixture to obtain 14.8 g of 3-(1,2,3,6-tetrahydro-4-pyridinyl)-5-methylthio-1H-indole in the form of yellow crystals metling at 210° C.

3 g of the said product were suspended in 300 ml of ethyl acetate and ethyl acetate saturated with gaseous hydrogen chloride was added thereto at 0° to 5° C. until the pH was acidic. The mixture was filtered and the recovered product was washed with ethyl acetate and dried under reduced pressure to obtain 3 g of 3-(1,2,3,6-tetrahydro-4-pyridinyl)-5-methylthio-1H-indole hydrochloride in the form of yellow crystals melting at 240° C.

Analysis: $C_{14}H_{17}N_2SCl$; molecular weight=280.82 Calculated: %C, 59.88; %H, 6.10; %N, 9.98; %Cl, 12.62; %S, 11.42. Found: C, 59.9; H, 6.1; N, 9.7; Cl, 12.6; S, 11.3.

EXAMPLE 2

Tablets were prepared containing 10 mg of 3-(1,2,3,6-tetrahydro-4-pyridinyl)-5-methylthio-1H-indole hydrochloride and sufficient excipient of lactose, starch, talc and magnesium stearate for a final tablet weight of 100 mg.

PHARMACEOLOGICAL DATA

A. Porsolt Test

The antidepressive activity was determined by the test by Porsolt [Arch. Int. Pharmacodyn. Therap., Vol. 229 (1977), p. 327] using groups of 5 male mice weighing about 20 g. The test compound was administered intraperitoneally and the mice were placed in a container filled with water from which the mice are not able to escape which provoked thier immobility. An antidepressant reduces the duration of this immobility and the compound of Example 1 strongly reduced immobility in mice at a dose of 4 mg/kg.

B. Antagonism Towards Catalepsy Caused By Prochlorpemazine

The test was effected on groups of 5 male rats weighing about 100 g and the test compound was administered intraperitoneally simultaneously with the intraperitoneal administration of 15 mg/kg of prochlorpemazine. The catalepsy was observed every hour for 7 hours following the test of crossing of homolateral paws [Boissier et al., Therapie, Vol. 18 (1963), p. 1257–1277-]with the following notations: The animal refused to cross the front paws with the homolateral rear paws (0); the animals accepted the crossing only for one side (0.5) and the animal accepted the crossing of both sides (1). The compound of Example 1 opposed catalepsy induced by prochlorpemazine at a dose of 0.2 mg/kg.

C. Antiemetic Activity

The antagonism to vomitting provoked by apomorphine was studied in dogs [CHen et al., J. Pharmac., exp. Therap., Vol. 93 (1959), p. 245–250] and the number of vomits provoked by subcutaneous injection of 0.1 mg/kg of apomorphine hydrochloride was determined for each animal 8 days before the test. The test compound in aqueous solution was subctuaneously administered at varying doses one half hour before the apomorphine hydrochloride. The compound of Example 1 reduced by 50% the vomits provoked of apomorphine at a dose of 1.5 mg/kg.

D. Acute Toxicity

The acute toxicity was determined on groups of 10 mice weighing about 20 g and the test compound was intraperitoneally administered at increasing doses. The mortality was determined 48 hours after the administration and the $LD_{50}$ doses for the compound of Example 1 was 150 mg/kg.

Various modifications of the products and processes of the invention may be made without departing from the spirit or scope thereof and it is to be understood that the invention is intended to be limited only as defined in the appended claims.

We claim:

1. A compound selected from the group consisting of 3-(1,2,3,6-tetrahydro-4-pyridinyl)-5-methylthio-1H-indole and its non-toxic, pharmaceutically acceptable acid addition salts.

2. A therapeutic composition for treating depression comprising an antidepressantly effective amount of at least one compound of claim 1 and a pharmaceutical carrier.

3. A method of inducing antidepressive activity in warm-blooded animals comprising administering to warm-blooded animals an amount of at least one compound of claim 1 sufficient to induce antidepressive activity.

* * * * *